US00PP28152P2

(12) United States Plant Patent
Hansen

(10) Patent No.: US PP28,152 P2
(45) Date of Patent: Jul. 4, 2017

(54) ***BUDDLEIA* PLANT NAMED 'LITTLE NUGGET'**

(50) Latin Name: ***Buddleia* hybrid**
Varietal Denomination: Little Nugget

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 14/999,591

(22) Filed: May 31, 2016

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Annette Para

(57) ABSTRACT

*Buddleia* 'Dark Dynasty' is a short, open, round-mounded, multi-stemmed, winter-hardy butterfly bush with many-flowered, compact, flowering, thyrse starting early and over a long season beginning mid-summer, from soil line to top of plant, with sweetly-fragrant magenta-purple flowers that are attractively offset by brilliant gold foliage.

1 Drawing Sheet

Botanical classification: *Buddleia* hybrid.
Variety denomination: 'Little Nugget'.

BACKGROUND OF THE PLANT

The present invention relates to the new and distinct butterfly bush plant in the Scrophulariaceae family, *Buddleia* 'Little Nugget' collected by Hans A. Hansen in the summer of 2012 at a wholesale perennial nursery in Zeeland, Mich., USA. 'Little Nugget' is the result of an ongoing breeding program conducted by the inventor. The goals for this program have been to produce improved, garden-worthy plants for the ornamental plant market with quality flowers, foliage and habit. The new plant, originally assigned breeder code H12-83-3, is a single plant selected from among multiple seedlings of an open pollination of the proprietary unreleased hybrid named *Buddleia* H10-97 (not patented) as the female or seed patent. H10-97 has *Buddleia weyeriana* and *B. davidii* in the background. The male parent is unknown, but may have been from any one of several proprietary or selected cultivars within the breeding field.

*Buddleia* 'Little Nugget' was first asexually propagated from a single select plant in 2014 by stem cuttings at the same nursery in Zeeland, Mich. The resultant asexually propagated plants have been found to be stable and true to type in successive generations of asexual reproduction.

No plants of *Buddleia* 'Little Nugget' have been sold, in this country or anywhere in the world, prior to the filing of this application, nor has any disclosure of the new plant been made prior to the filing of this application except that which may have been disclosed within one year of the filing of this application and was either derived directly or indirectly from the inventor.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of 'Little Nugget'.

The nearest comparison plant is *Buddleia* 'Evil Ways' (not patented) which has a taller habit and shorter inflorescence. *Buddleia* 'Santana' U.S. Plant Pat. No. 12,383 is variegated and has a yellow to chartreuse leaf margin along with a medium green leaf center.

*Buddleia* 'Little Nugget' is a unique winter-hardy butterfly bush different from all other *Buddleia* cultivars known to the inventor based on the following combined traits:

1. Winter-hardy shrub, with multiple-stemmed, branched, short, open, round-mounded habit.
2. Many-flowered compact thyrse starting early and over a prolonged season beginning mid-summer and continuing until frost from soil line to top of plant.
3. Dark flowers of magenta purple petal faces with small orange throat.
4. Lanceolate foliage of brilliant gold.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
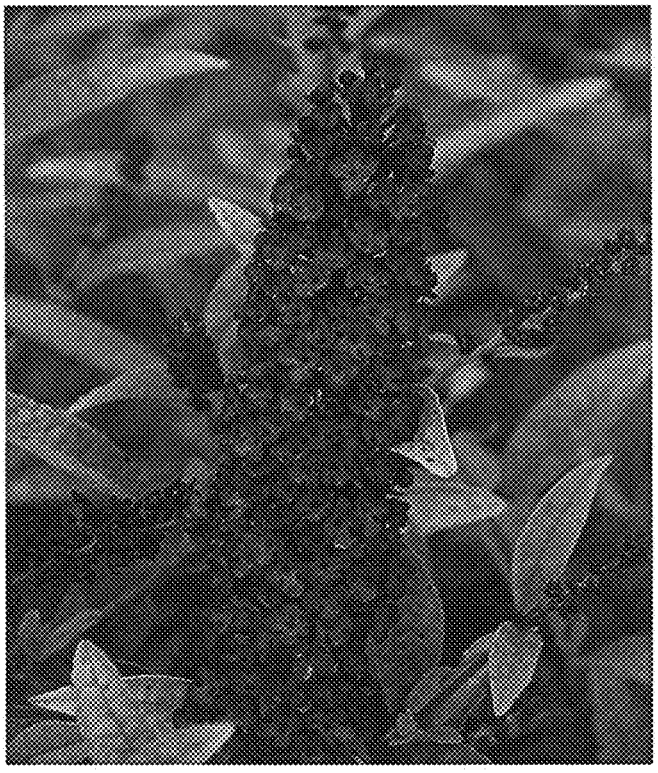
FIG. 1 shows a close-up of the flowers with buds near apex.
Figure 2:
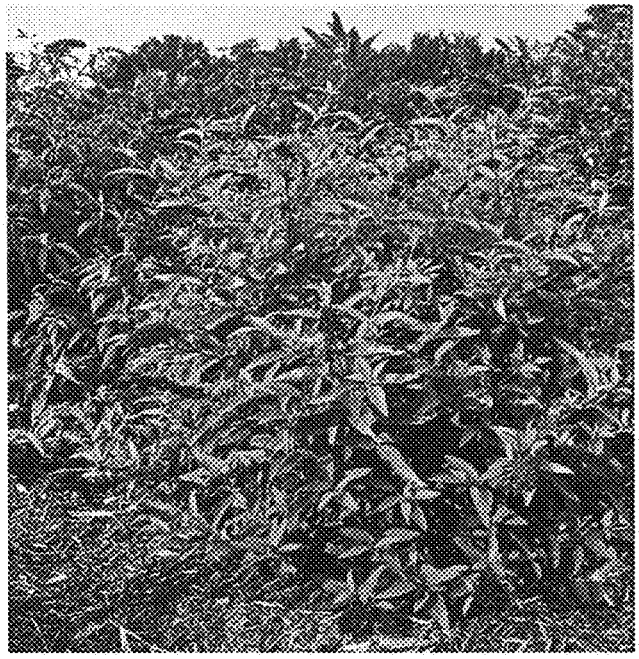
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Little Nugget', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Unreleased proprietary hybrid H10-97 (not patented) as the female or pod parent times an unknown open-pollination as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8-10 weeks to finish and flower in a four-liter container from a 25 mm liner; Plant vigor is very good.

Plant description:

*Plant shape and habit*.—Winter-hardy, herbaceous, semi-woody, well-branched shrub with about 10 thick upright and branched main stems producing a compact rounded mound about 100 cm tall and about 120 cm wide.

*Stem*.—Rounded and woody in lower portion terete in cross section with exfoliating bark; younger upper portion puberulent and quadrangular in cross section with ridges in corners; strong and flexible; average about 90 cm tall from soil line to just below terminal flowers, and about 1.0 cm diameter at the base; before distal flowers about 9 branches per main stem extending at about 45° to 60° angle down from main stem.

*Stem color*.—Distal portion just below flowers nearest RHS N186C, and in about the basal 20 cm blend between RHS 161A and RHS 165B with striations nearest RHS 200C; RHS N199B.

*Plant size*.—Unpinched plant with stems flowering to about 100 cm tall; overall plant about 120.0 cm wide.

*Internode*.—About 10 nodes per stem below flowers, average internode length about 7.5 cm on unpinched plant; upper internodes slightly more elongated than lower internodes.

*Node color*.—Same as surrounding stem.

Foliage description: Opposite, decussate; serrulate; puberulent abaxial and sparsely puberulent adaxial; elliptic to lanceolate with attenuate base and acute apex; no foliar fragrance detected.

*Leaf blade size*.—Up to about 12.0 cm long and about 4.0 cm wide, average about 7.5 cm long and about 2.5 cm wide; becoming smaller in distal portion of stem.

*Foliage color*.—Young expanding leaf adaxial side nearest RHS N144A, young expanding abaxial nearest RHS 145C; mature leaves adaxial side regions nearest RHS 144A and RHS N144B, mature abaxial nearest RHS 148D; very young leaves with light blushing toward apical half of margin nearest RHS 187B on both surfaces.

*Veins*.—Reticulate; abaxial raised, adaxial slightly impressed.

*Vein color*.—Young expanding adaxial veins nearest RHS 144A, abaxial young expanding veins nearest RHS 145C; mature adaxial veins nearest RHS 144A and RHS N144B; abaxial veins nearest RHS 145C; very young adaxial veins nearest RHS 144A, very young abaxial veins nearest RHS 187B.

*Petioles*.—Glaucous and puberulent abaxial and adaxial; partially applanate adaxial to abaxial; average size about 5.0 mm long and about 1.0 mm wide at the point of attachment to stem.

*Petiole color*.—Nearest RHS 144A adaxial and RHS 145C abaxial.

*Inflorescence description*.—Glomerate thyrse consisting of about 400 self-cleaning salverform flowers; to about 17.5 cm long and about 4.0 cm across; early, beginning in mid-July and continuing until late October in Michigan; attitude outward to slightly upward.

*Buds*.—Elongated clavate, apex rounded; one day prior to opening about 9.5 mm total length and about 2.5 mm diameter in club, throat about 1.2 mm diameter in throat and about 7.0 mm long.

*Bud color*.—Between RHS 77A and RHS 83A in club portion and tube portion nearest RHS 71A.

*Sepals*.—Four, proximal two-thirds connate, adpressed to corolla tube; acute apex; glabrous adaxial and pubescent abaxial; margin entire, edentate; fused in about the basal 2.0 mm and split in about the terminal 1.5 mm; forming a corolla about 3.5 mm long and about 1.0 mm across; individually less than about 1.0 mm wide at point of fusion.

*Sepal color*.—Adaxial nearest RHS 138C, abaxial between RHS 145A and RHS 139C heavily tinted with nearest RHS 186C.

*Flowers fragrance*.—Pleasantly and distinctly sweet.

*Flower attitude*.—Upward and outward.

*Lastingness of inflorescence*.—About 8 to 10 days.

*Lastingness of individual flower*.—About 3 to 5 days.

*Petals*.—Four; glabrous; fused into salverform with typically straight cylindrical tube about 8.0 mm long and 1.0 mm diameter, and a flattened face about 6.0 mm across; petal blade rounded with crenate margin; blade to about 2.5 mm across and about 3.0 mm long from fused face.

*Petal color*.—Adaxial tube center nearest RHS 168C, tube base nearest RHS 155D, face between RHS 83B and RHS 79D; abaxial tube nearest RHS 180B with slight tinting of RHS 71A, abaxial petal blades between RHS 83B and RHS 79D.

*Gynoecium*.—Pistil: one; about 3.2 mm long. Style: short, round, glabrous; about 1.5 mm long and less than 0.2 mm diameter; color nearest RHS 155C blushed in the apical two-thirds with nearest RHS 187B. Stigma: oblong, minutely puberulent; about 0.2 mm in diameter and less than 0.4 mm long; color nearest RHS 144B. Ovary: superior; globose; about 1.0 mm across at base and about 1.4 mm tall; distally tapering to style; color between RHS 144C and RHS 144B.

*Androecium*.—Filaments: not produced or very short. Anthers: typically four; oblong; introise; adnate to about mid-point of corolla tube; about 1.0 mm long and about 0.5 mm wide; color nearest RHS 158A. Pollen: numerous, globose, less than 0.1mm across; color nearest RHS 158A.

*Pedicel*.—Short, puberulent; about 1.0 mm long and less than 0.5 mm diameter; color lighter than RHS 146D.

*Peduncle*.—Quadrangular, pubescent, flexible and strong; flowering portion to about 13.5 cm long.

*Peduncle color*.—Nearest RHS 148C with tinting of nearest RHS N187B.

*Fruit*.—Sparse fruit set; oblong with acute apex; glabrous, bi-valved, applanate, septicidal capsule; about 6.0 mm long and about 2.0 mm across and 2.0 mm thick.

*Fruit color*.—As maturing nearest RHS 162D; when mature and dehiscing nearest RHS 164B.

*Seed*.—Elongated ellipse with sharply acute ends; less than about 2.0 mm long and about 0.1 mm diameter in center.

*Seed color*.—Nearest RHS 200A.

Disease resistance: Resistance has been noted to deer browsing. Other resistance beyond that of known butterfly bush cultivars has not been observed. The plant grows best with plenty of moisture and adequate drainage, but is able to tolerate some drought when mature.

Hardiness at least from USDA zone 6 through 10.

I claim:

1. A new cultivar of winter-hardy butterfly bush *Buddleia* plant named 'Little Nugget' as herein illustrated and described, especially suitable for potted plant culture, landscaping as a specimen or en masse or as cut flower purposes.

* * * * *